United States Patent
Blackman et al.

(10) Patent No.: US 10,933,217 B2
(45) Date of Patent: Mar. 2, 2021

(54) CATHETER ASSEMBLY HAVING COUPLEABLE PORTIONS AND METHODS OF USE

(71) Applicants: Gurvan Edmond Blackman, Robbinsville, NJ (US); David Christopher Feldstein, Haddonfield, NJ (US)

(72) Inventors: Gurvan Edmond Blackman, Robbinsville, NJ (US); David Christopher Feldstein, Haddonfield, NJ (US)

( * ) Notice: Subject to any disclaimer, the term of this patent is extended or adjusted under 35 U.S.C. 154(b) by 109 days.

(21) Appl. No.: 16/221,507

(22) Filed: Dec. 15, 2018

(65) Prior Publication Data

US 2019/0184134 A1 Jun. 20, 2019

Related U.S. Application Data

(60) Provisional application No. 62/599,247, filed on Dec. 15, 2017.

(51) Int. Cl.
*A61M 25/00* (2006.01)
*A61M 25/06* (2006.01)
*A61M 39/00* (2006.01)

(52) U.S. Cl.
CPC .... *A61M 25/0026* (2013.01); *A61M 25/0014* (2013.01); *A61M 25/0028* (2013.01); *A61M 25/0097* (2013.01); *A61M 25/0625* (2013.01); *A61M 39/00* (2013.01); *A61M 25/0043* (2013.01); *A61M 2025/0034* (2013.01); *A61M 2025/0037* (2013.01)

(58) Field of Classification Search
CPC .. A61M 2025/0034; A61M 2039/1016; A61M 2039/1027; A61M 25/0014; A61M 25/0097; A61M 39/00; A61M 39/105
See application file for complete search history.

(56) References Cited

U.S. PATENT DOCUMENTS

2017/0043126 A1* 2/2017 Jones ................ A61M 39/105

* cited by examiner

*Primary Examiner* — Deanna K Hall
(74) *Attorney, Agent, or Firm* — Wei & Sleman LLP (57) ABSTRACT

A catheter assembly includes a flexible catheter having a lumen, a hub having a body including a proximal end and a distal end, the body defining a passageway extending from the proximal end to the distal end, the hub being coupled to one end of the catheter, and the passageway of the hub being in fluid communication with the lumen of the catheter, and a coupler including a base coupleable to and detachable from the hub, the base being coupled to at least one introducer assembly, each of the at least one introducer assembly including a port, a tubing and a hollow needle.

20 Claims, 8 Drawing Sheets

CATHETER ASSEMBLY HAVING COUPLEABLE PORTIONS AND METHODS OF USE

CROSS-REFERENCE TO RELATED APPLICATIONS

This application claims priority to U.S. Provisional Application Ser. No. 62/599,247, entitled "CATHETER ASSEMBLY HAVING COUPLEABLE PORTIONS AND METHODS OF USE," filed Dec. 15, 2017, which is incorporated by reference herein in its entirety.

FIELD OF THE DISCLOSURE

The present disclosure relates to catheters having connectors for use in medical settings. More particularly the present disclosure relates to compact catheters with connectors having detachable portions for certain applications such as long-term use.

BACKGROUND OF THE DISCLOSURE

Medical procedures may require the use of devices for intravenous access for prolonged periods of time. In some cases, percutaneous catheters may be used to access the patient's vasculature. Examples of such catheters may include central venous catheters (i.e., central lines), peripherally inserted central catheters (PICCs), midlines, and dialysis/apheresis catheters.

Such catheters may be bulky and cumbersome to use. Additionally, due to their size, such catheters may bring discomfort to the patient. For example, in a typical tunneled dialysis catheter, a substantial portion of the catheter, measuring up to 15-20 cm is exposed and will hang loosely from a patient's chest or leg. These limitations of the catheters also make them prone to breakage, damage and inadvertent removal when a portion of the device becomes hooked on the patient's clothing, blankets, or other medical devices. Such a long exposed portion of a catheter may also lead to an increase in infection rate.

Additionally, in some cases, such devices may need to be utilized for long-term care such as, for example, care for longer than thirty days. In such examples, these bulky devices may be uncomfortable both physically and psychologically for the patient.

SUMMARY OF THE DISCLOSURE

In some embodiments, a catheter assembly may include a flexible catheter having a lumen, a hub having a body including a proximal end and a distal end, the body defining a passageway extending from the proximal end to the distal end, the hub being coupled to one end of the catheter, and the passageway of the hub being in fluid communication with the lumen of the catheter, and a coupler including a base coupleable to and detachable from the hub, the base being coupled to at least one introducer assembly, each of the at least one introducer assembly including a port, a tubing and a hollow needle.

In some embodiments, a method of administering at least one of a medicine, a liquid, or a contrast to a patient may include inserting a guidewire into a body of the patient, and delivering a flexible catheter having a lumen over the guidewire into the body, the flexible catheter being coupled to a hub having a self-sealing septum, and a body defining a passageway, the passageway of the hub being in fluid communication with the lumen of the catheter.

BRIEF DESCRIPTION OF THE DISCLOSURE

Various embodiments of the presently disclosed catheter connectors are disclosed herein with reference to the drawings, wherein.

Various embodiments of the present invention will now be described with reference to the appended drawings. It is to be appreciated that these drawings depict only some embodiments of the invention and are therefore not, to be considered limiting of its scope.

DETAILED DESCRIPTION

Despite the various improvements that have been made to catheters and connectors, conventional devices suffer from some shortcomings as described above.

There therefore is a need for further improvements to the devices, systems, and methods of manufacturing catheters. Among other advantages, the present disclosure may address one or more of these needs.

As used herein, the term "proximal," when used in connection with a component of a catheter assembly, refers to the end of the component closest to the physician when the catheter is inserted in a patient, whereas the term "distal," when used in connection with a component of a catheter assembly, refers to the end of the component farthest from the physician when the catheter is inserted in a patient.

Likewise, the terms "trailing" and "leading" are to be taken as relative to the operator (e.g., physician) of the catheter assembly. "Trailing" is to be understood as relatively close to the operator, and "leading" is to be understood as relatively farther away from the operator.

To lower the possibility of damage, removal and malfunction of a catheter, and to improve patient comfort and safety, an improved catheter assembly may be formed which includes portions that easily decouple from one another.

Figure 1A:
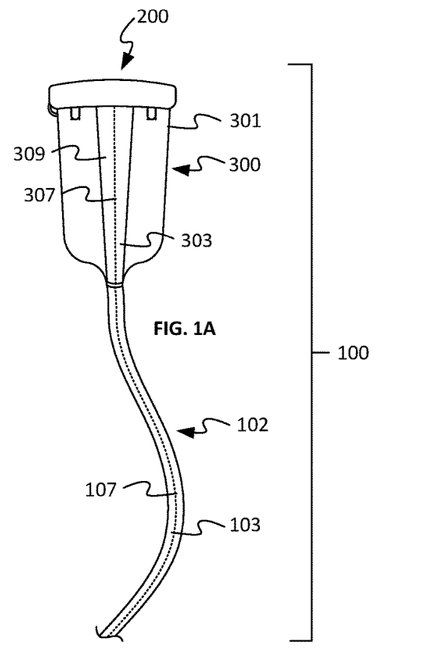
FIG. 1A is a schematic side view of a hub coupled to catheter, the hub having a cap in the closed position.

FIG. 1A show a hub-catheter assembly 100 having a catheter 102 defining at least one lumen 103 therethrough. Catheter 102 may be in the form of a plastic or other polymeric tubing have a predetermined length based on its usage. For example, catheter 102 may be 5 cm to 60 cm long. In some examples, the catheter may be between 20 to 40 cm. Additionally, catheter 102 may have a diameter of between about 3 french and about 30 french, or may be configured for use within the peripheral and/or central vasculature (e.g., internal or external jugular, subclavian, axillary, brachial, basilic, cephalic, common femoral, and saphenous veins). In some examples, the diameter of catheter 102 is between 3 and 30 french. Alternatively, a catheter assembly may include a catheter 102 in the form of a tubing that is capable of being cut down to the desired length by the physician or operator. Optionally, catheter 102 may be divided into two sections via wall 107 that runs along the length of the catheter to separate two or more materials being delivered through the catheter, where mixing of the materials is undesirable. In such embodiments, two lumens 103 are formed in catheter 102. Alternatively, multiple walls 107 may be formed so that catheter 102 includes one, two, three, four or more lumens 103 as shown in FIG. 1D which shows cross-sections of such catheters. In examples of multiple lumens 103, the lumens 103 may be formed of the same or a different length than each other by placing exit ports 104 along varying lengths of the catheter adjacent the distal end of the catheter (FIG. 1C). Thus, where lumens 103 of different lengths are used, materials may be delivered to different locations within the patient.

A proximal end of catheter 102 is attached to hub 300 having a body 301, which defines at least one passageway 303 therethrough. Body 301 may be formed of a biocompatible polymer or a biocompatible metal. Each passageway 303 may be in fluid communication with a lumen 103 of catheter 102. Additionally, in some examples, passageway 303 may have an increasing diameter from its distal end adjacent the catheter to its proximal end adjacent cap 200, which lies flat on top of hub 300. As shown, a partition 307 divides passageway 303 into two portions 309, each portion being in fluid communication with one lumen 103 of catheter 102. The number of portions 309 of passageway 303 may be equal to the number of lumens 103 of catheter 102. Thus, one, two, three, four or more passageways may be formed to complement a catheter having the same number of lumens. Additionally, the configuration and shape of the passageways may be complementary to the configuration of the lumens of the catheter. For example, two passageways may be disposed next to each other to match a catheter having two opposing lumens. In other examples, three passageways may be spaced 120 degrees apart to complement the shape of the catheter having three lumens. In another example, four passageway are formed in a configuration that complements the four-lumen configuration of the catheter shown in FIG. 1D.

Figure 1B:
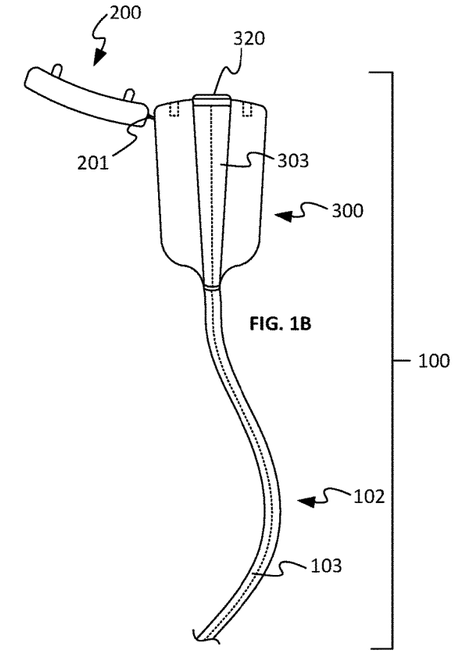
FIG. 1B is a schematic side view of the hub of FIG. 1A with the cap being positioned in the open position.
Figure 1C:
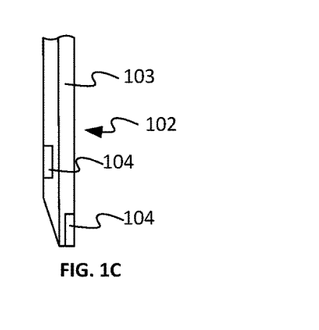
FIG. 1C is a schematic representation of an example of a catheter having multiple lumens and exit ports.
Figure 1D:
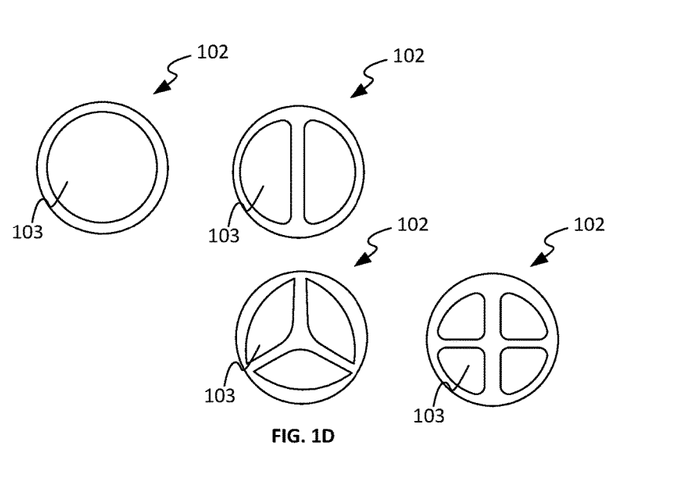
FIG. 1D shows are schematic cross-sections of catheters having different numbers of lumens.

Cap 200 may be coupled to hub 300 via a hinge 201, and may alternate between a closed position (FIG. 1A) and an open position (FIG. 1B). In some examples, cap 200 may be formed of the same or a different material than hub 300 (e.g., a plastic or a metal), and hinge 201 may include a plastic material or a tether attached to both the hub and the cap to keep the cap from being lost when not in use. As shown in FIG. 1B, moving cap 200 to the open condition reveals septum 320 of hub 300.

Figure 2A:
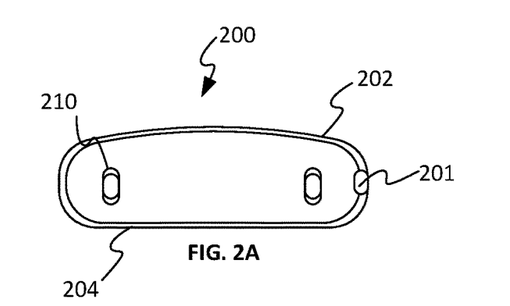
FIGS. 2A and 2B are bottom and top views of the cap of FIGS. 1A-B.
Figure 2B:
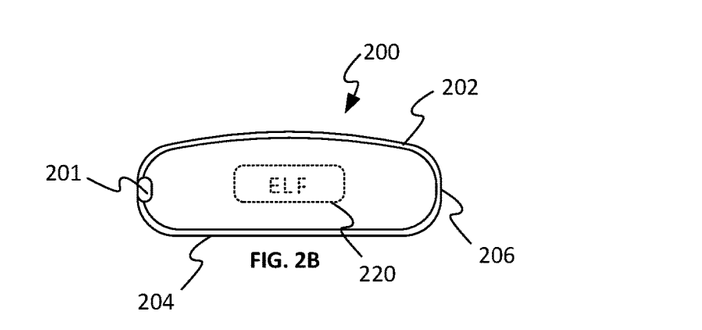
Figure 3:
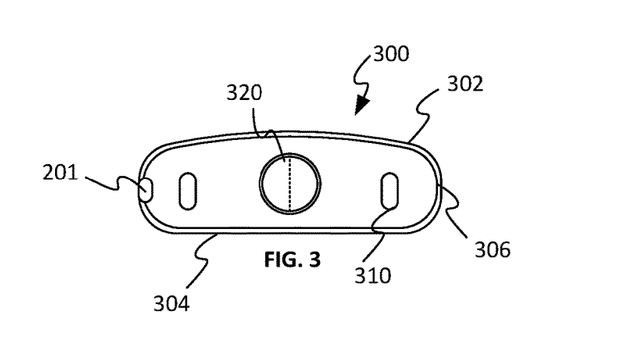
FIG. 3 is a top view of the hub of FIGS. 1A-B, the hub having a septum.

Turning to FIGS. 2A-3, the details of cap 200 and hub 300 will now be described. As shown in FIGS. 2A-B, cap 200 includes a curved edge 202 opposite a flat edge 204, and two side edges 206 defining a perimeter. Cap 200 further includes two male members 210 in the form of prongs or legs that extend away from the bottom surface of the cap for coupling to a portion of the hub. Cap 200 may includes an indicator 220 on its top surface that includes information of the device, such as manufacturer, model, or to indicate compatibility with other systems. In the example shown, the top of cap 200 includes the initials "ELF" to indicate that the device is compatible with other Extension-Leg-Free devices.

Hub 300 may have a similar top profile to cap 200 and may include curved edge 302 opposite a flat edge 304 and a pair of side edges 306 forming a perimeter. Hub 300 may be arranged so that flat edge 304 contacts and lays flat on the patient's skin (e.g., on the forearm).

Hub 300 may include a pair of female receptacles 310 to accept the male members 210 of cap 200. In at least some examples, female receptacles 310 may include a recess, indentation or notch and male member 210 may be friction fit within female receptacle 310 to releasably secure the cap to the hub in the closed condition as shown in FIG. 1A. Additionally, it will be understood that the number of male members and the number of female receptacles may be increased or decreased as desired. For example, in one example, only a single male member 210 is coupleable to a single female receptacle 310. In other examples, three or more pairs of male members and female receptacles are used to couple the hub to the cap.

Hub 300 may also have a self-sealing septum 320 at its center. In some examples, self-sealing septum may include a silicone membrane, or other similar fluid impermeable material that is capable of being pierced by a needle and sealing itself when the needle is removed. Cap 200 may cover and protect self-sealing septum 320 when the septum is not in use so that the septum remains clean and undamaged.

Figures 4A, 4B:
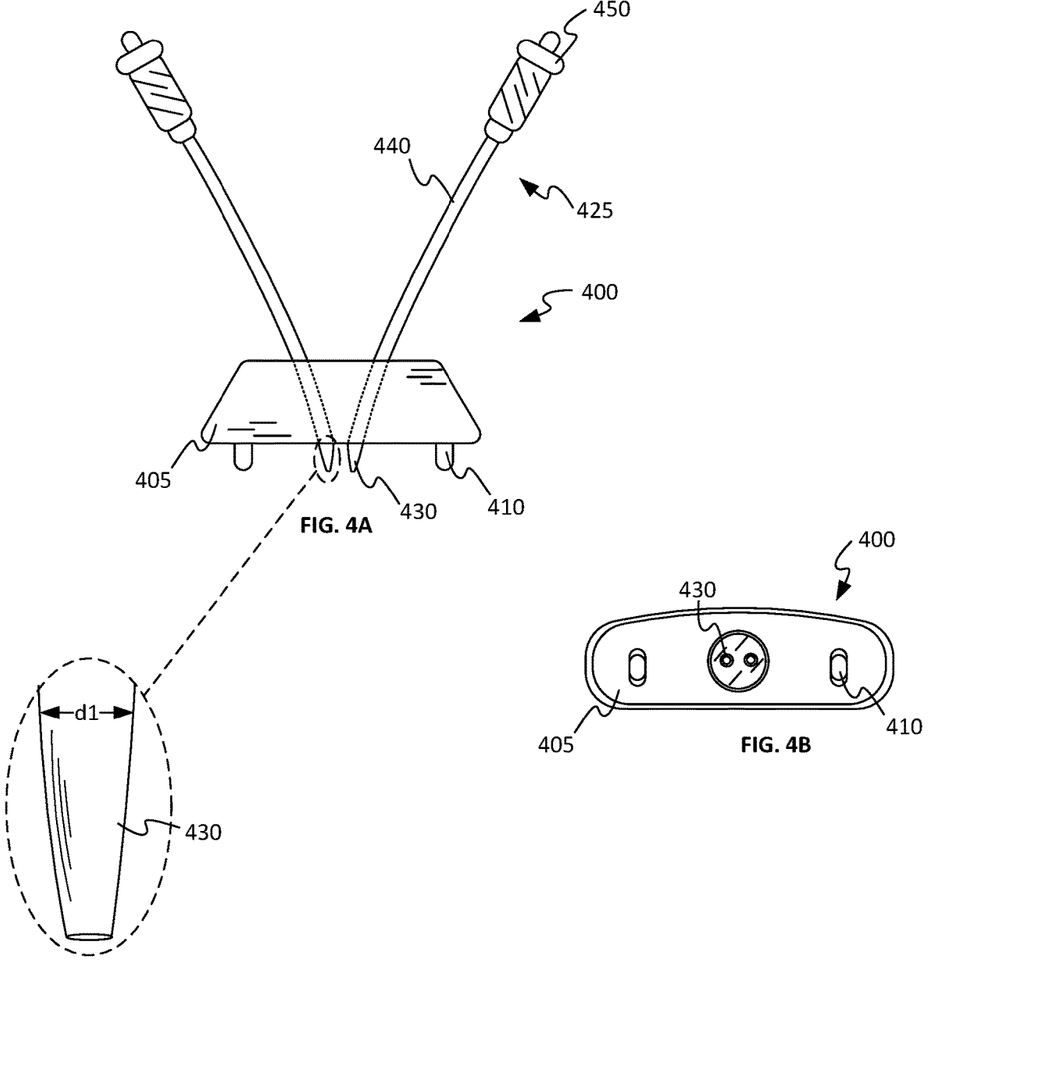
FIG. 4A is a schematic side view of a coupler for use with the hub of FIG. 1A.
FIG. 4B is a schematic bottom view of the coupler of FIG. 4A.

FIG. 4A shows a coupler 400 for use with hub 300. Coupler 400 generally includes a base 405 and an introducer assembly 425. Base 405 may be substantially similar in width to cap 200, and may formed of the same materials discussed above with reference to the hub and the cap. Base 405 may include male members 410 projecting from its bottom surface that are similar to male members 210 of cap 200, male members 410 and male members 210 both being alternatively releasably coupleable to the same female receptacle 310.

Attached to base 405 and extending through base 405 are a pair of introducer assemblies 425. Each introducer assembly 425 is arranged as a unit including a needle 430, a tubing 440 and a connector (e.g., Luer connector) 450. As shown, coupler 400 includes two introducer assemblies 425. It will be understood that coupler 400 may instead include a single introducer assembly 425, or three, four or more introducer assemblies 425. Needle 430 may be hollow and in fluid communication with the interior of tubing 440 and connector 450 such that a material introduced through connector 450 via a syringe or other device may travel through the interior of connector 450, tubing 440, through base 405, and hollow needle 430.

Needle 430 may have a taper at its distal end. In other words, needle 430 may have an outer diameter d1 that gradually decreases away from base 405. In at least some examples, dl is between 0.5 mm and 10 mm at its widest, and narrows down to between 0.1 mm and 5 mm. This size of the needle may allow it to easily pierce septum 420, while being small enough to allow resealing of the septum after its removal.

FIG. 4B shows the bottom of base 405. As shown, base 405 includes the pair of male members 410 on either side of a central ring, which includes needles 430. The arrangement of male members 410 and needles 430 mirrors that of female receptacles 310 and septum 320 on hub 300. In some examples, the number of male members 410 of coupler 400 is equal to the number of male members 210 of cap 200.

Figure 5A:
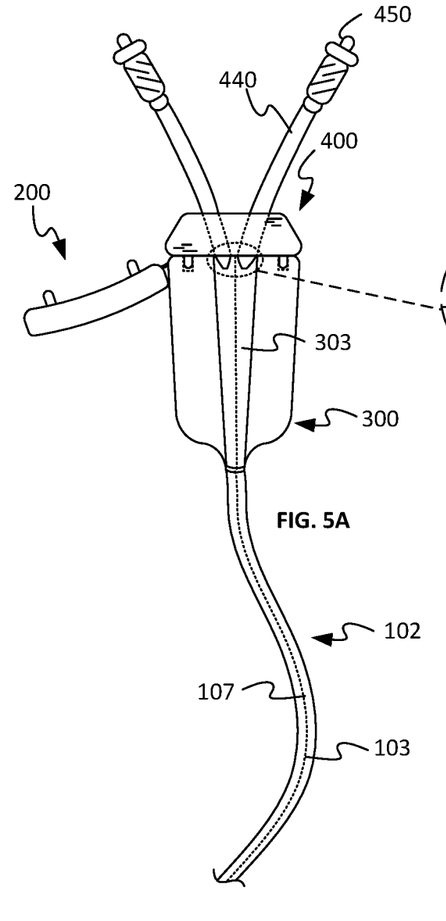
FIG. 5A is a schematic side view of a catheter assembly having the coupler of FIG. 4A attached to the hub of FIG. 1A.
Figure 5B:
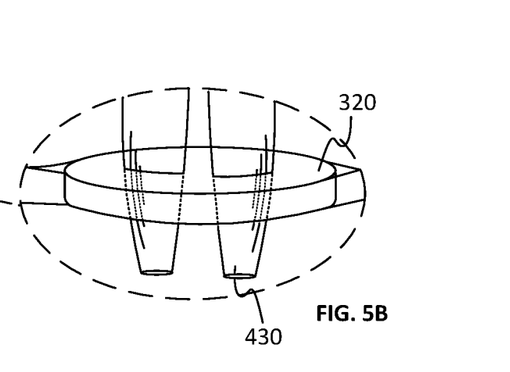
FIG. 5B is an enlarged portion of FIG. 5A showing a portion of the coupler piercing a portion of the hub.

FIG. 5A shows coupler 400 being attached to hub 300. As shown, cap 200 is in the open position and is disposed away from the hub 300 to reveal the interface of hub 300. Male members 410 of coupler 400 mate with female receptacles 310 of hub 300 to secure the two bodies together. Additionally, as shown in FIG. 5B, hollow needles 430 pierce through self-sealing septum 320 of hub 300 so that the needles extend through the septum and into passageway 303. In this manner, a material introduced through connector 450 may travel through tubing 440 across base 405 and into passageway 303, lumen 103 of catheter 102 to be delivered to the patient.

Figure 5C:
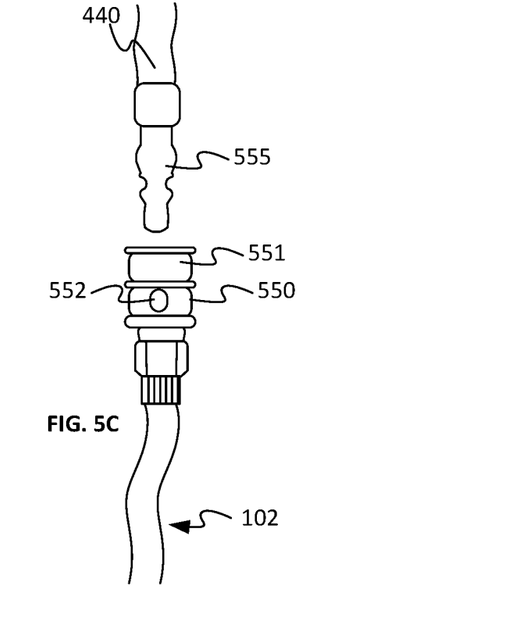
FIG. 5C is a schematic side view of another example of a connector.

In one variation, shown in FIG. 5C, a quick-connect water or fluid coupling is used instead of a needle-septum combination. Quick-connect water coupling may include a fluid-tight coupling mechanism having a female end 550 and a male end 555. Female end 550 may be joined to catheter 102 and a male end 555 may be joined to tubing 440 and connector 450 (e.g., a luer connector). In some examples, female end 550 may be configured to receive male end 555 and to form a fluid-tight lock after receiving the male end. This lock may be simply achieved by pushing the male end into the female end. In some examples, female end 550 includes a spring-loaded fitting 551 such that pulling the fitting toward the catheter allows the release of male member 555 from within female end 550. Alternatively, a button 552 on the female end may be used to release the male end 555.

Figure 6A:
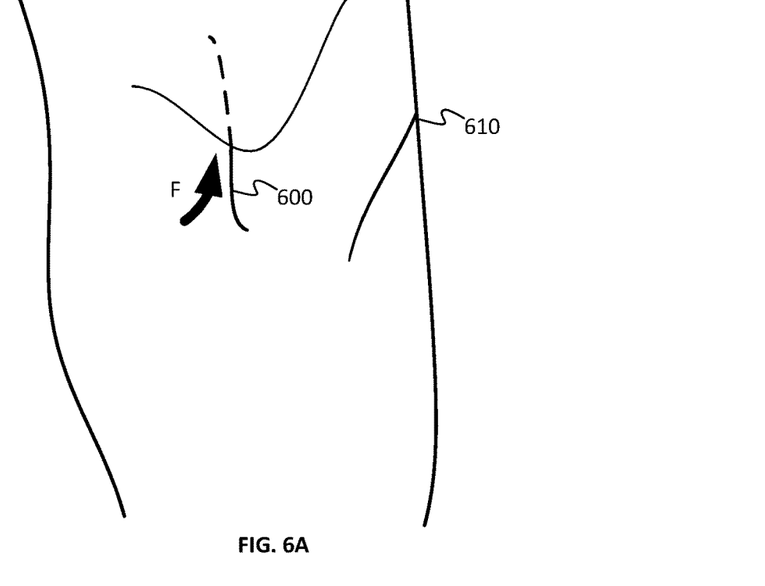
FIGS. 6A-C are schematic representations of the catheter assembly during use.
Figure 6B:
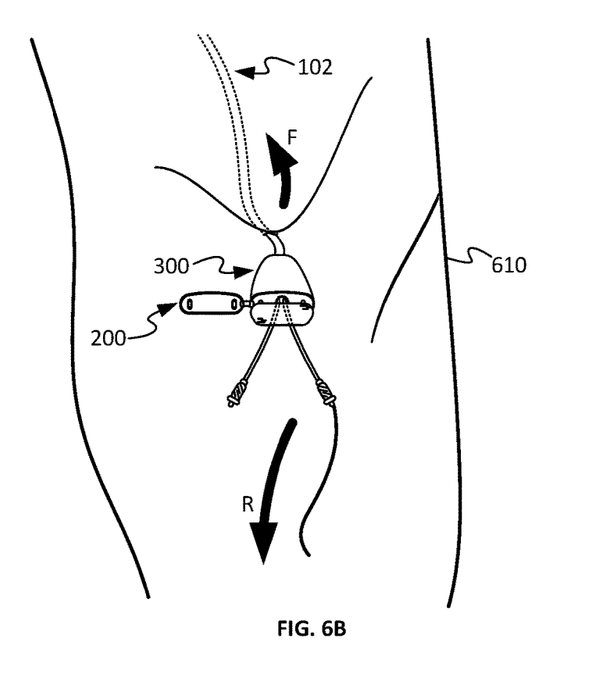

In use, a guidewire 600 may be inserted into the patient's body 610 (e.g., a patient's forearm near the elbow) in direction "F" (FIG. 6A). Catheter 102 may be inserted over the guidewire 600 in the direction "F" into the patient's body and hub 300 may be disposed outside of the patient's body (e.g., on the patient's forearm) (FIG. 6B). Guidewire 600 may then be removed by being pulled in the reverse direction "R" (FIG. 6B) so that it exits through the self-sealing septum via the hollow needle 430 and connector 450.

Figure 6C:
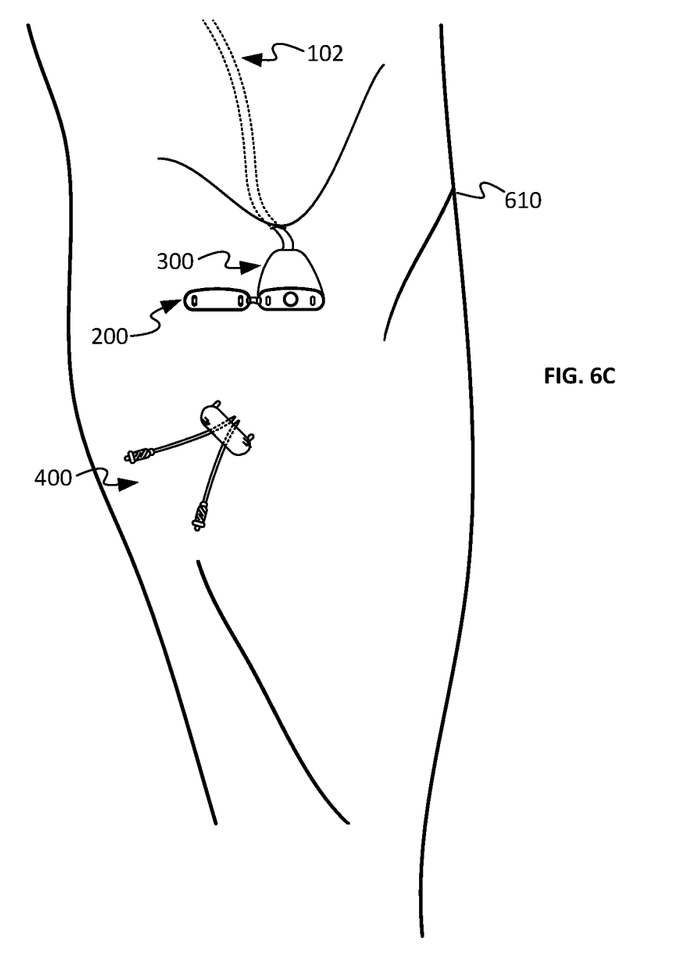

One or more couplers 400 may be used when needed to deliver a therapy to the patient. When not in use, only the hub 300 and its associated catheter remains with the patient. However, when a medicament, fluid or other material (e.g., contrast) needs to be delivered to the patient, the cap 200 over hub 300 may be opened to reveal the septum of hub 300, and a coupler 400 may be used to deliver the material across the septum (FIG. 6C). In couplers having multiple introducer assemblies, multiple materials (e.g., fluids, medicaments, contrasts, etc.) may be delivered to the patient simultaneously, each material being deliver through a designated connector via a designated lumen of catheter 102.

After the coupler 400 is used, it may be disengaged from hub 300 and disposed of, and cap 200 may be returned to the closed position. In such a way, coupler 400 is only attached to the patient when in use, and not unnecessarily carried by the patient at all times. The same or a different coupler 400 may be used in the next instance that a material is to be delivered to the patient.

Figure 7:
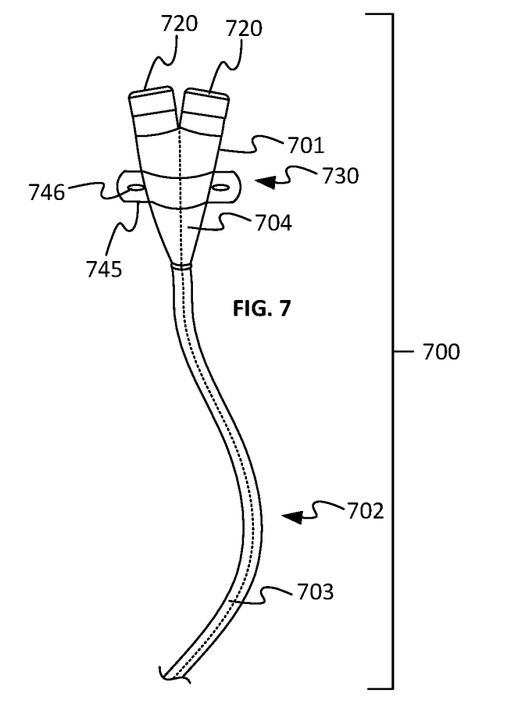
FIG. 7 is a schematic side view of another embodiment of a catheter assembly.

FIG. 7 is a schematic side view of another embodiment of a catheter assembly 700. Catheter assembly 700 includes a catheter 702 defining a lumen 703 therethrough. Catheter 702 may be coupled at one end to a generally triangular hub 730 having a body 701. Body 701 may be hollow so as to define a passageway 704 in fluid communication with lumen 703. Body 701 may have a set of generally increasing diameters from one end that is coupled to the catheter, to a second end that is coupled to septums 720. Septums 720 may be formed of similar materials and configurations as septum 320 and configured to be pierced with a hollow needle, such as described above. Alternatively, instead of septum 720, body 701 may be coupled to other types of couplers, such as standard-sized Luer tapers. Though two septums 720 are shown, it will be understood that hub 730 may include a single septum (or coupler) or more than two septums (e.g., three, four, five, six or more septums or couplers). Additionally, a hub 730 may include a mixture of different types of couplers (e.g., one or more septums, and one or more clean connectors so that different introduction ports are useful for different functions). Hub 730 may further be coupled to an anchoring mechanism 745 having a pair of wings with eyelets 746. Eyelets 746 may be used to attach the device to the patient's skin via sutures, or via adhesive or some other method.

Figure 8A:
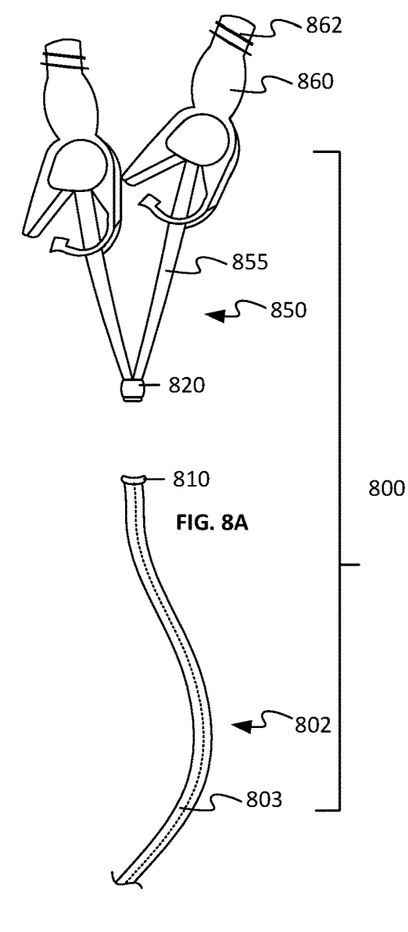
FIGS. 8A and 8B are schematic perspective views of yet another embodiment of a catheter assembly.
Figure 8B:
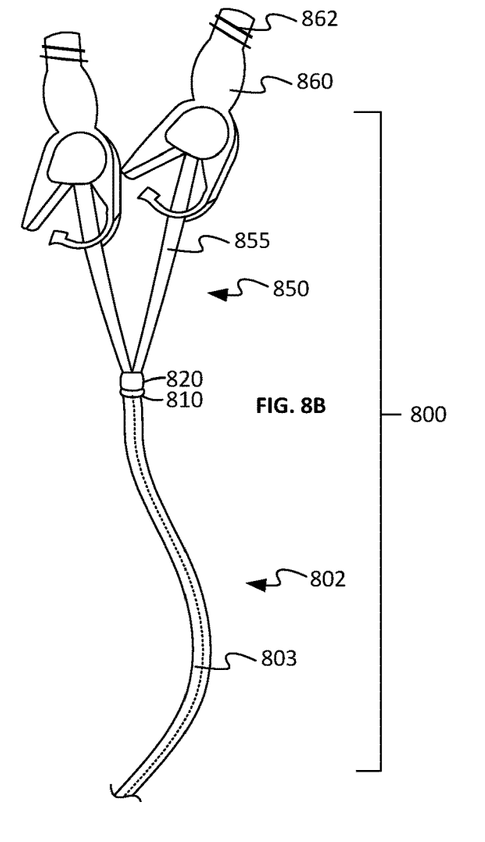

FIGS. 8A-B shows yet another variation of a catheter assembly. Catheter assembly 800 is similar to catheter assembly 700 in that it includes a catheter 802 having a lumen 803 and a hub 850. In this case, catheter 802 terminates in a first coupler 810 so that this portion is separable from hub 850. Likewise, hub 850 includes a second coupler 820 that is mateable with first coupler 810. In at least some examples, first coupler 810 may be a female connector and second coupler may be a male connector that mates with the female coupler. The two couplers may alternatively be formed of needle-self-sealing septum combination similar to that described above.

Two tubes 855 branch out from second coupler 820, each terminating in conventional end couplers 860 having mating elements 862. In some examples, end couplers 860 may include a Luer Taper/Lock mechanism, or other systems for small-scale fluid fittings used for making leak-free connections between a male taper fitting and its mating female port on medical and laboratory instruments including, but not limited to hypodermic syringe tips, needles, stopcocks, etc.

Instead of conventional couplers 860, each tube 855 may instead terminate in a septum such as those described above. Additionally, though two tubes and couplers are shown, any number of tubes/couplers may be used, such as a single tube/coupler or three or more tube/coupler assemblies.

In one variation of the embodiments of FIGS. 8A and 8B, couplers 870 and 872 may be used instead of couplers 810,820. Coupler 870 may be connected to catheter 802 and includes external threading 871, while coupler 872 may be connected to tubes 855 to conventional couplers 860, coupler 872 being internally threaded. Additionally, tubes 855 may terminate in tapered portions 890 so that they are easily received within the lumen of catheter 802. To connect the two portions together, tapered portions 890 of tubes 855 may be pushed into the respective lumen of catheter 802 and coupler 872 may be screwed onto and over coupler 870 so that a water-tight seal is formed.

Figure 8C:
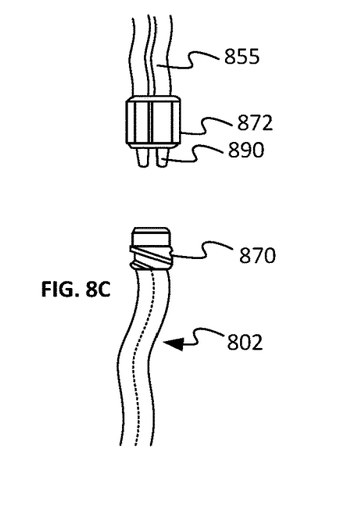
FIG. 8C is a schematic representation of another example of a pair of couplers having a luer mechanism.

As seen in FIGS. 8A and 8B, when couplers 810,820 (or 870,872) are joined together to create a fluid-tight seal, a physician or healthcare provider may inject a substance through end couplers 860 into catheter 802 via tubes 855. Conversely, when a fluid or medicament is not being delivered to a patient, hub 850 including tubes 855 and end couplers 860 may be removed so that only catheter 802 is disposed with the patient's body and only first coupler 810 (or coupler 870 in the case of the embodiment of FIG. 8C) is disposed outside the body, the first coupler being accessible by the physician. In this manner, the portion of the device extending outside the patient's body is minimized, and a hub is only used when needed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invent on as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A catheter assembly comprising:
   a flexible catheter having at least one lumen;
   a hub having a body including a proximal end and a distal end, the body defining a passageway extending from the proximal end to the distal end, the hub being coupled to one end of the catheter at the proximal end and having a first surface at the distal end, the first surface having at least one female receptacle spaced away from the passageway, and the passageway of the hub being in fluid communication with the at least one lumen of the catheter; and
   a coupler including a base coupleable to and detachable from the hub, the base including at least one male member, projecting from a second surface, that is releasably coupleable to the at least one female receptacle, the base being coupled to at least one introducer assembly, each of the at least one introducer assembly including a connector, a tubing and a hollow needle spaced away from the at least one male member.

2. The catheter assembly of claim 1, wherein the passageway of the hub terminates in a self-sealing septum that covers the passageway but not the at least one female receptacle.

3. The catheter assembly of claim 2, wherein the self-sealing septum includes a silicone membrane.

4. The catheter assembly of claim 1, wherein the at least one female receptacle includes a recess, and the at least one male member includes a prong.

5. The catheter assembly of claim 1, wherein the at least one male member is friction fit within the least one female receptacle.

6. The catheter assembly of claim 1, wherein the at least one introducer assembly includes two introducer assemblies.

7. The catheter assembly of claim 2, wherein the hollow needle is spaced to align with the self-sealing septum of the hub when the hub and the base are coupled together, the hollow needle being configured, sized and arranged to pierce through the self-sealing septum and allow the septum to seal after the hollow needle is removed.

8. The catheter assembly of claim 2, wherein the hollow needle is configured to extend completely through the self-sealing septum to deliver a material across the self-sealing septum.

9. The catheter assembly of claim 8, wherein the material includes at least one of a medicine, a liquid or a contrast.

10. The catheter assembly of claim 1, wherein the hollow needle has an outer diameter of between 0.5 mm to 1.0 mm.

11. The catheter assembly of claim 1, wherein the hollow needle has a taper.

12. The catheter assembly of claim 1, further comprising a cap coupled to the hub via a hinge, the cap including at least one male member for coupling to the at least one female receptacle of the hub.

13. The catheter assembly of claim 1, wherein the tubing and the hollow needle define a conduit in fluid communication with the passageway of the hub and one of the at least one lumen of the catheter.

14. The catheter assembly of claim 2, wherein the passageway of the hub has a plurality of diameters, the plurality of diameters gradually increasing from a first end closer to the catheter to a second end closer to the self-sealing septum.

15. The catheter assembly of claim 1, wherein the at least one female receptacle includes two female receptacles disposed on two sides of the passageway, and the at least one male member includes two male members.

16. The catheter assembly of claim 15, wherein the flexible catheter comprises at least a first lumen having a first exit port and a second lumen having a second exit port and wherein the first exit port of the first lumen extends farther than the second port of the second lumen.

17. A method of administering at least one of a medicine, a liquid, or a contrast to a patient including:
    inserting a guidewire into a body of the patient; and
    delivering a flexible catheter having a lumen over the guidewire into the body, the flexible catheter being coupled to a hub having a self-sealing septum and at least one female receptacle spaced away from the self-sealing septum, and a body defining a passageway, the passageway of the hub being in fluid communication with the lumen of the catheter.

18. The method of claim 17, further comprising the step of coupling a first coupler to the hub, the first coupler having a base and at least one introducer assembly coupled to the base, each of the at least one introducer assembly including a port, a tubing and a hollow needle.

19. The method of claim 18, wherein coupling the first coupler to the hub includes piercing the self-sealing septum of the hub with the hollow needle of the first coupler or mating a male member of the first coupler to the at least one female receptacle of the hub.

20. The method of claim 17, further comprising (i) decoupling the first coupler from the hub after use, and disposing of the first coupler while keeping the catheter within the body of the patient, (ii) coupling a second coupler to the hub after decoupling the first coupler from the hub, and (iii) decoupling the second coupler from the hub after use, and disposing of the second coupler while keeping the hub in place.

* * * * *